US00PP21091P3

(12) United States Plant Patent
Nonomura

(10) Patent No.: US PP21,091 P3
(45) Date of Patent: Jun. 22, 2010

(54) ***BOTRYOCOCCUS* ALGAE PLANT NAMED 'NINSEI'**

(50) Latin Name: *Botryococcus braunii*
Varietal Denomination: Ninsei

(76) Inventor: Arthur M. Nonomura, 4904 North Green Drive E., Litchfield Park, AZ (US) 85340

( * ) Notice: Subject to any disclaimer, the term of this patent is extended or adjusted under 35 U.S.C. 154(b) by 690 days.

(21) Appl. No.: 11/429,531

(22) Filed: May 5, 2006

(65) Prior Publication Data

US 2006/0265800 P1 Nov. 23, 2006

Related U.S. Application Data

(60) Provisional application No. 60/678,711, filed on May 6, 2005.

(51) Int. Cl.
*A01H 5/00* (2006.01)

(52) U.S. Cl. ..... Plt./395

(58) Field of Classification Search ..... Plt./395
See application file for complete search history.

(56) References Cited

U.S. PATENT DOCUMENTS

| | | | | |
|---|---|---|---|---|
| 4,383,039 | A | 5/1983 | Leavitt | 435/107 |
| PP6,169 | P | 5/1988 | Nonomura | Plt./89 |
| 5,476,787 | A | 12/1995 | Yokoyama et al. | 435/262.5 |
| 2006/0252138 | A1 * | 11/2006 | Nonomura | 435/166 |
| 2006/0265800 | P1 * | 11/2006 | Nonomura | Plt./395 |

FOREIGN PATENT DOCUMENTS

WO WO 2006121950 A1 * 11/2006

OTHER PUBLICATIONS

Chu, S. P. 1942. J. Ecol. 30: pp. 284-325; "The Influence of the Mineral Composition of the Medium on the Growth of Planktonic Algae".
Phytochemistry, vol. 28, No. 11, pp. 3043-3046, 1989; Zheng Huang et al.; "Isoshowacene, AC31 Hydrocarbon From *Botryococcus braunii* Var. Show A".
J.Org. Chem. 1988, 53, 5390-5392; Zheng Huang et al.; "Isobraunicene, Wolficene, and Isowolficene. New Cyclic 1'-3 Fused Isoprenoids from *Botryococcuc braunii*".
J.Org. Chem. 1988, 53, 4089-4094; Zheng Huang et al.; "Braunicense. Absolute Stereochemistry of the Cyclohexane Ring".
J.Am.Chem.Soc. 1988, 110, pp. 3959-3964; "Braunicene, a Novel Cyclic C32 Isoprenoid from *Botryococcus braunii*".
Food and Feed Crops of the United States, Second Edition, Revised; GM Markle, et al.
Index of Garden Plants; The New Royal Horticultural Society Dictionary; Mark Griffiths.
Center for Phycological Documentation; Index Nominum Algarum.
Jpn. J. Phycol. (Sorui) 36: 285-291, Dec. 10, 1998; Arthur Michio Nonomura; *Botryococcus braunii* var. (*Chlorophyceae*) from Berkeley, California, United States of America.
Arch Microbiol (1984) 140: 101-106; Masayuki Ohmori et al.; "*Botryococcus braunii* carbon/nitrogen metabolism as affected by ammonia addition".
J. Phycol. 21, 388-396 (1985); Fred R .Wolf et al.; "Growth and Branched Hydrocarbon Production in a Strain of *Botryococcus braunii* (*Chlorophyta*)".
Western Fertilizer Handbook.
Jian Qin et al; "Bio-Hydrocarbons from Algae"; Australian Government Rural Industries Research and Development Corporation, Feb. 2005.
S.J. Lee et al.; "Effects of harvesting method and growth stage on the flocculation of the green alga *Botryococcus braunii*"; Letters in Applied Microbiology, vol. 27, 1998 pp. 14-18.
P.Metzger et al.; "*Botryococcus braunii*: a rich source for hydrocarbons and related ether lipids"; Appl. Microb. Biotechnol, vol. 66, 2005 (published online 2004).
R.C. Hochmuth et al; "Hydroponic Nutrient Effluent—A Recoverable Energy Resource", University of Florida Cooperative Extension Service, Apr. 1999 p. 1-4.
A.Torres et al; Characterization of surface n-alkanes and fatty acids of the epiphytic lichen *Xanthoria parietina*, its photobiont a green alga trebouxia sp., and its mycobiont, from the Jerusalem Hills, Eur. J. of Biochem, vol. 270, 2003, pp. 2120-2121 especially.
Process Biochemistry 40 (2005) 3125-3131; C. Dayananda et al.; "Effect of media and culture conditions on growth and hydrocarbon production by *Botryococcus braunii*".
Office Action dated Jun. 13, 2008 (in related U.S. Appl. No. 11/429,536).
Office Action dated Oct. 20, 2008 (in related U.S. Appl. No. 11/429,536).

* cited by examiner

*Primary Examiner*—Annette H Para
(74) *Attorney, Agent, or Firm*—Nields, Lemack & Frame, LLC

(57) ABSTRACT

A novel variety of *Botryococcus* distinct from the previously cultured variety in color, biochemistry, size, shape, and habit.

3 Drawing Sheets

CROSS-REFERENCE TO RELATED APPLICATIONS

This application claims priority of provisional application Ser. No. 60/678,711, filed May 6, 2005, the disclosure of which is hereby incorporated by reference.

LATIN NAME OF GENUS AND SPECIES OF PLANT CLAIMED:

*Botryococcus* genus, spcies braunii.

BACKGROUND OF THE INVENTION

The present invention is a novel and distinct variety provided as a potential source of hydrocarbons.

For decades, *Botryococcus braunii* has been suggested as a potential source of liquid transport fuels and although the hydrocarbon content has been as high as 30% of biomass, such high hydrocarbon content occurs during a period of dwindling green pigmentation, the loss of chlorophyll concomitant with a resting phase of exceedingly slow growth rates. In the practice of solar irradiated mass culture, optimization of green chlorophyll pigmentation would be beneficial for the efficient capture of light for continuous rapid growth and may be accomplished by vegetative breeding to increase pigmentation. The novel variety of the present invention is anatomically distinguished by the presence of an apical depression in cells of its colonies.

BRIEF SUMMARY OF THE INVENTION

In the present invention, I have discovered, isolated and grown a novel variety of *Botryococcus braunii* with a deeper hue of green pigmentation and physiological and morphological distinctions from its mother variety. The features of the novel variety are suitable for culture in vitro under illuminated environments typical of mass production.

Stock cultures were taken from bottom-dwelling colonies of *Botryococcus braunii* variety 'Showa', claimed by U.S. Plant Pat. No. 6,169, maintained on standard phycological enhancement media known by those in the art. Sterile test tubes (20 mm×150 mm) with friction fit stainless steel caps were each filled with up to 20 ml of media and steam sterilized twice for 60 minutes. The cultures were stepped up to larger volumes until approximately 1 million submerged green colonies were collected from the bottom of 1 liter glass flasks. Harvested colonies were concentrated into 5 ml with overnight settling. The supernatant was decanted and colonies were resuspended in 15 ml of aqueous culture medium. Transferred cultures were produced in 10 replicates and placed in the dark. Control cultures were transferred into equal volumes of conventional phycological media.

Single colonies were identified visually for hydrocarbon-vesicle content and selected manually with micropipettes.

Maintenance of cultures for long durations under high light intensity illumination ranging between 500 to 1700 $\mu E/m^2/sec$ PAR, 8–20 h light, at 25–35° C. was preferred in any of a number of conventional maintenance media, preferably, Chu 13 that was designated to *Botryococcus* based on limnological analyses (Chu, S. P. 1942. J. Ecol. 30:284-325); however, it was found to lack a full complement of definable trace mineral nutrients. 'Showa' nutrients from U.S. Plant Pat. No. 6,169 are incorporated by reference herein, and provided as a control in experiments. Supplementation with 1% to 3% carbon dioxide or bicarbonates (e.g., 10 mg/ml blended potassium bicarbonate and ammonium bicarbonate) enhanced growth rates under the highest light intensities. Phycocolloids were infused with 1% to 20% calcium carbonate. On replication of colonies, additional 'Showa' medium was metered into maintenance cultures as nutrients were exhausted. The floating colonies of the strain of the present invention are characterized by greater than 22% content of mixed botryococcenoid branched hydrocarbons ($C_nH_{2n-10}$, n=30–37) preferably when under the previously identified requirements of exposure to high light intensities and carbon dioxide.

As the variety of the present invention also sheds oils from the colonial matrix when induced with mild pressure, as for example, from hydrological shear, the colonies are suited for continuous harvest of botryococcenes from reusable biomass.

DETAILED BOTANICAL DESCRIPTION

Description of Processes for Selection

Figure 1:
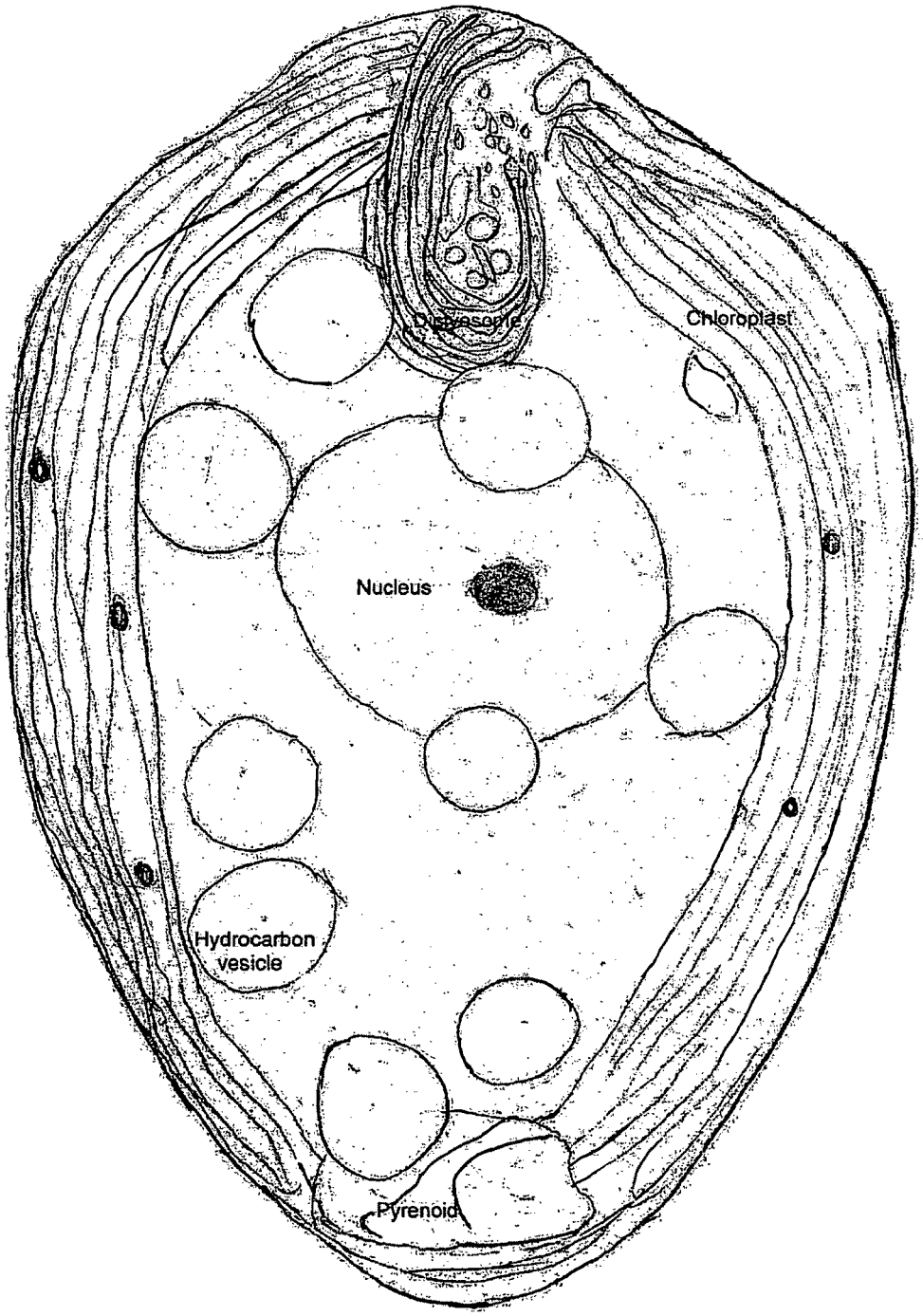
FIG. 1 illustrates a 5 μm breadth by 8 μm height cell of a colony showing an ovoid cell containing nine round hydrocarbon vesicles, a dictyosome, a nucleolus, and a parietal chloroplast.

The present invention comprises the novel and distinct 'Ninsei' that was deposited at the American Type Culture Collection (Post Office Box 1549, Manassas, Va. 20108) in March 2006 and assigned ATCC No. PTA-7441. This Trebouxiophyceaen is hereinafter referred to as 'Ninsei'.

Ninsei was isolated as a mutagenized clone by irradiating colonies on 1% agar supplemented with minerals in sterile plastic Petri dishes at $LD_{50}$ 15 watt UV, 1 cm, for 10 minutes. This period of UV exposure killed all other organisms on the plates. Survivors were selected for depth of green hue, tolerance to 50 ppm zinc niche, and hydrocarbon content. The single originating clonal isolate replicated rapidly under 24 h/d light with buffered nutrients to fall within a range of pH 7±0.5.

Colonies of 'Ninsei' were archived in sterile test tubes with stainless steel caps, each filled with up to 10 ml of media and steam sterilized for 30 minutes. Single colony replicates were, thereafter, re-selected for growth in 50 ppm to 70 ppm $Zn^{+2}$ and visually identified for high hydrocarbon-vesicle content through micromanipulation and selection with micropipettes. Colonies on $Zn^{+2}$ were isolated for hydrocarbon production by placing selections in the dark to eliminate artifacts of flotation from oxygen bubbles. A single colony selection was visually confirmed to contain over a dozen hydrocarbon-vesicles and was deemed suitable for micropropagation. Culture conditions provided up to 1500 $\mu E/m^2/sec$ PAR, 8–24 h light at 20–30° C. Supplementation with nutrients and a source of assimilable carbon such as 1% to 5% carbon dioxide gas or carbonate (e.g., 10 mg/ml potassium carbonate or potassium bicarbonate), increased growth with hydrocarbon synthesis substantially, especially, when under the highest light intensities. The preferred environment for maintenance of 'Ninsei' required buffering by appropriate concentrations of nutrient salts and carbonate adjusted to pH 7.

Colonies of 'Ninsei' are variably-shaped groups of cells held together in cups of tough sporopollenin-like matrices. Depth of color depends on the light regime, density of culture and physiological state of the colonies. All color designations are made with reference to the Munsell Book of Color. Normal healthy colonies range from 5 GY 7/8 to 2.5 GY 8/12 on the Munsell color chart and these 'Ninsei' colonies, fully pigmented with chlorophylls, may float at the surface of growing cultures with high hydrocarbon content that may reflect golden overtones.

The 'Ninsei' variety of the present invention is characterized at an average green hue of 2.5 GY 6/10±50% on the Munsell color chart for healthy colonies. In contrast, 'Showa' is described as a yellow hue of 2.5 Y 7/8 on the Munsell color chart. Vegetative reproduction resulting in increased colony count is maintained as long as there is chlorophyll content to reflect 2.5 GY hues. No growth has been observed in the Y through YR Munsell Color range, but conversion of carbon stores to hydrocarbon may continue up into the YR brown state of decline. Flotation is concomitant with growth of botryococcenes branched hydrocarbons ($C_nH_{2n-10}$, n=30–37).

Figure 2:
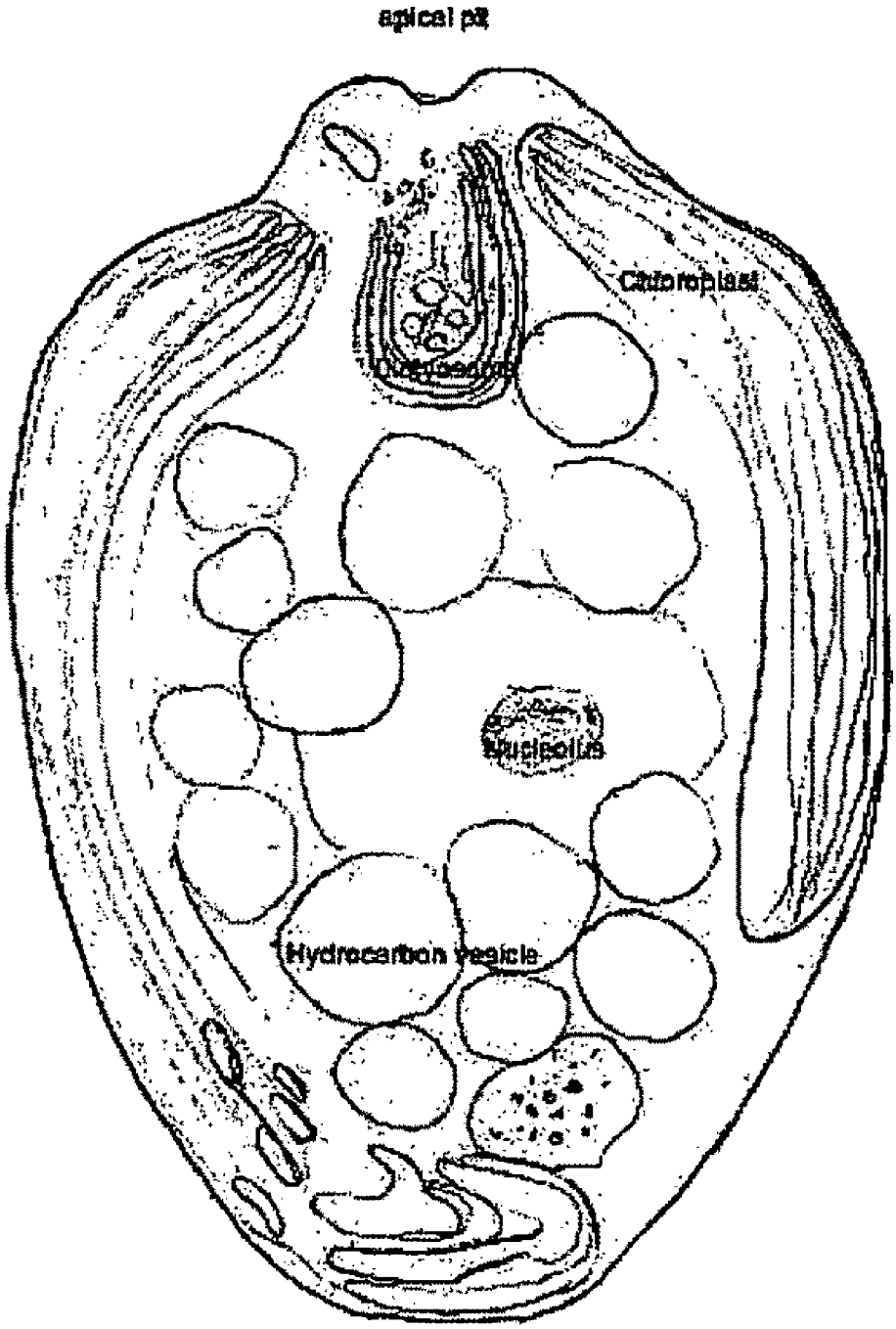
FIG. 2 illustrates the apical pit observable in a cell of a colony.
Figure 3:
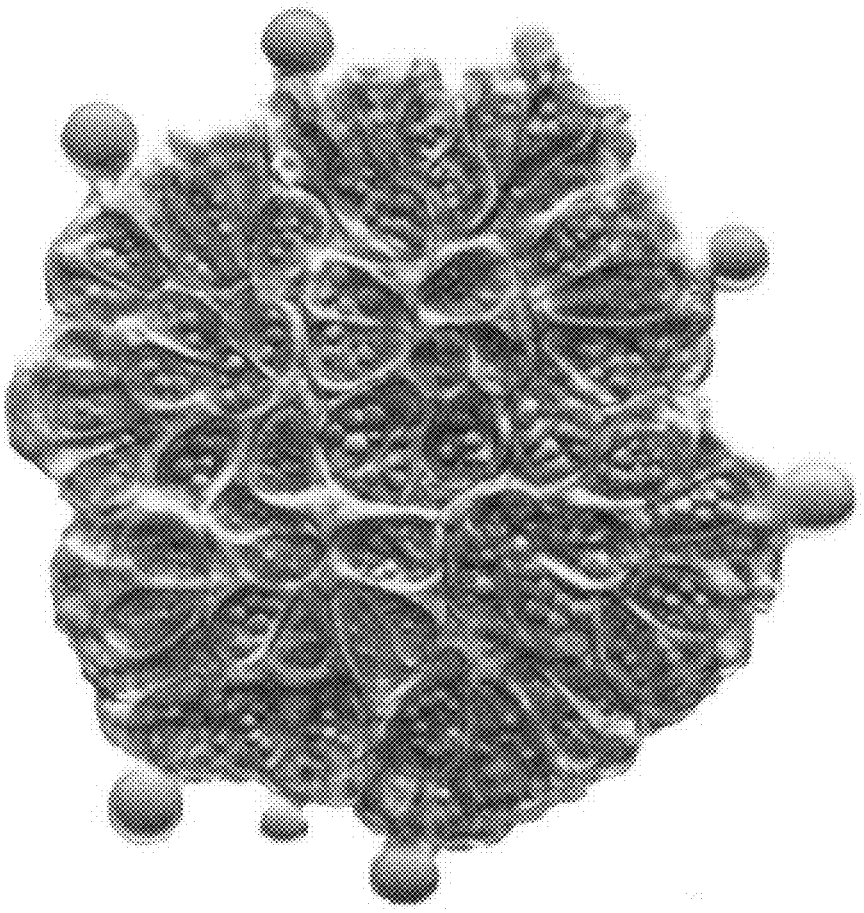
FIG. 3 is a microphotograph of a green hydrocarbon-rich colony showing ovoid protuberant cells, each containing five and more round hydrocarbon vesicles. At the perimeter are seven hydrocarbon droplets extruded from the colony by pressure from the glass cover slip.

When released from the colonial matrix, cells of the colonies are 5 μm to 10 μm spheres often pressed by neighboring cells into irregular shapes. Within the colony, the cells are wedged into almond shapes between neighboring cells. Neither 'Showa' nor 'Ninsei' has a sexual phase in their life cycles. Deposits of hydrocarbon, 0.1 μm to 1 μm in diameter, are present in the cytoplasm, wall, and matrix. An occasional cell of 'Ninsei' exhibits a depression at the outer tip of the cell, the apical pit (see FIG. 2), that most frequently appears in cells with few hydrocarbon vesicles. The depression may, in fact, be an opening from which results the secretion of oils. The name of the strain is, in fact, derived from the urn forms of cells with open tops, reminiscent of shapes of large ceramic wares by the artist of Kyoto, ca. 1600 AD, Ninsei.

The secretion of oils may have a protective function, for when the colonies dwells at the surface, they are fully exposed to ultraviolet radiation. Hydrocarbon-rich colonies effectively block UV and a film of hydrocarbon floating at the surface would function as a sun block. The hydrocarbons may block sufficient PAR to prevent photoinhibition and is thus consistent with occupation of the superficial mud niche.

The colonial unit is spherical and aggregates of units contribute to the formation of irregular grape-like clusters observed in large colonies. During rapid growth of the novel strain, colonies are generally smaller than 'Showa's' 50 μm colonies. In 'Ninsei', smaller colonies may range from 10 μm to 45 μm in diameter. Colonies of 100 or more cells are predominantly composed of irregularly shaped units that fragment into roughly rounded colonies.

'Ninsei' is visually distinguishable from other strains of the variety by its deep green hue, small size attributable to rapid growth, cell structure, and niche. Defined growth medium for the strain of the present invention will usually include major and secondary and trace metal plant nutrients. The preferred formulae provide balanced primary fertilizers, nitrogen, phosphoric, and potash; secondary nutrients, Ca, S, and Mg; and micronutrients such as, Fe, Mn, Zn, Cu, B, Mo, Co, and Ni. Suitable chelants for these nutrients include EDTA, HEEDTA, NTA, DTPA, EDDHA, citrate, and the like. Consistent with culture practices of the present invention, the most highly preferred medium that originated from the present inventor for maintenance with rapid growth of hydrocarbons is KwiK, listed below, a highly concentrated nutrient formulation from the patent application entitled "Methods and Compositions for Growth of Hydrocarbons in *Botryococcus* sp.", now Ser. No. 11/429,536 and filed simultaneously herewith and incorporated herein by reference. 'Ninsei' was found to grow hydrocarbons best under at least about 500 μE/m$^2$/sec light intensity and tolerate unusually high concentrations of soluble $Zn^{+2}$ ranging from 0.08 mM to 0.36 mM $Zn^{+2}$.

KwiK Medium, Adjusted to pH 7 with Phosphate Buffer

| Component | Concentration Range | Archival Concentration |
|---|---|---|
| $KH_2PO_4$ | 80–800 ppm | 272 ppm |
| $K_2HPO_4$ | 80–1000 ppm | 348 ppm |
| $KNO_3$ | 500–2500 ppm | 800 ppm |
| Chelants | 80–800 ppm | 200–750 ppm |
| $MgSO_4$ | 1–1000 ppm | 125 ppm |
| $Ca^{+2}$ | 1–800 ppm | 88 ppm |
| Mn | 0.1–3 ppm | 0.1 ppm |
| Fe | 0.3–10 ppm | 0.5–9 ppm |

-continued

| Component | Concentration Range | Archival Concentration |
|---|---|---|
| Cu | 0.01–1 ppm | 0.02 ppm |
| B | 0.2–2 ppm | 0.2 ppm |
| $Zn^{+2}$ | 0.3–50 ppm | 0.2 ppm |
| Mo | 0.001–0.05 ppm | 0.02 ppm |
| Co | 0.001–0.05 ppm | 0.002 ppm |

Colonies grow particularly well in the above supplemented solid media, such as when dissolved in an aqueous 0.5% to 1.5% agar gel; cloaking with 0.5% to 3% carbon dioxide; under continuous (24 h light per day) or periodic (e.g., 16:8 h LD) PAR light exposure; under 500 μE/m$^2$/sec to 1700 μE/m$^2$/sec light intensity in high density cultures; and temperatures up to 35° C. Exposure of 'Ninsei' to high intensity light, nutrients for optimal photosynthesis, 2 mM to 100 mM phosphates, at least about 3 ppm Fe, and 0.2 ppm to 45 ppm $Zn^{+2}$ nutrient concentration with 1% to 3% carbon dioxide, accelerated metabolism of hydrocarbons and is a characteristic of 'Ninsei'.

'Ninsei' is identifiable by its mixed botryococcenoid branched hydrocarbons ($C_nH_{2n-10}$, n=30–37); likewise, an unusual $C_{32}H_{54}$ cyclic isoprenoid distinguishes 'Showa' to U.S. Plant Pat. No. 6,169. The 'Ninsei' strain is identifiable by its content of several hydrocarbon structures including, braunicenoids, wolficenoids, and showacenoids; the biochemical fingerprint analyses understood by those in the art. The presence of the collected $C_{30}$ to $C_{37}$ botryococcenoid series within 'Ninsei' is uniracial, providing a consistent source of quick power as the chemistry of choice for renewable transport fuels.

'Ninsei' is further distinguishable from other Trebouxiophyceans by its buoyant response in the presence of ammonium salts; in contrast, 'Showa' stopped synthesis of hydrocarbons when exposed to 1 mM ammonium chloride. When transferred from KwiK and into the defined preferred ZaP hydrocarbon enrichment medium, an original medium given below, the colonies of 'Ninsei' rose to the meniscus overnight. The preferred ZaP formula was derived from 50 mM ammoniacal nitrogen. Consistent with culture practices of the present invention, the most highly preferred medium for buoyant growth of hydrocarbon-rich colonies is by ZaP, an ammoniacal variation of ZiP, both original media from the above-referenced patent application Ser. No. 11/429,536. 'Ninsei' was found to tolerate unusually high concentrations of soluble $Zn^{+2}$ ranging from 0.08 mM to 0.36 mM $Zn^{+2}$. The preferred method for making ZiP is to mix and sterilize a solution of 160 mM to 400 mM total phosphates and add equal volumes of the phosphate solution to pre-sterilized KwiK resulting in 80 mM to 200 mM total phosphates ZiP solutions with chelated nutrients.

ZaP Competitive Enrichment Medium, Adjusted to pH 6.8 with Phosphate Buffer

| Component | Concentration Range | Preferred Concentration |
|---|---|---|
| $KH_2PO_4$ | 0.136 ppm - 2% | 1.36% |
| $(NH_4)_2HPO_4$ | 0.132 - 2% | 1.32% |
| $KNO_3$ | 0.1% to 1% ppm | 0.8% |
| Chelants | 80–800 ppm | 200–750 ppm |
| $MgSO_4$ | 1–1000 ppm | 125 ppm |
| $Ca^{+2}$ | 1–880 ppm | 88 ppm |
| Mn | 0.5–10 ppm | 0.2 ppm |

-continued

| Component | Concentration Range | Preferred Concentration |
|---|---|---|
| Fe | –10 ppm | 7 3 ppm to 8 ppm |
| Cu | 0.01–1 ppm | 0.02 ppm |
| B | 0.2–2 ppm | 0.2 ppm |
| $Zn^{+2}$ | 2–70 ppm | 36 ppm |
| Mo | 0.001–0.05 ppm | 0.02 ppm |
| Co | 0.001–0.05 ppm | 0.002 ppm |

Other species of *Botryococcus* have been described as aquatic, whereas, 'Ninsei' occupies the mud niche, showing its most rapid growth at the surface of nutrient-supplemented solid media. When common major elements of its niche, N, P, K, Fe, Mg, Mn, Ca, and Zn, were presented to 'Ninsei' at up to about 10-fold and greater concentrations than in conventional hydroponic media, an exclusive environment was created in the present invention for the competitive advantage requisite for mass culture of the singular strain. 'Ninsei', thereby, was artificially selected to be the fittest to survive in an environment that would be otherwise too harsh for other life. Physical separation of one population from another by occupation of a niche to the exclusion of another lends to the biological definition of speciation; therefore, 'Ninsei' represents a novel strain that occupies a niche at the water's edge that had not previously been defined in culture.

What is claimed is:

1. A new and distinct variety of *Botryococcus braunii* algae plant named 'Ninsei', as herein illustrated and described.

* * * * *